US005624260A

United States Patent [19]
Wilcox et al.

[11] Patent Number: 5,624,260
[45] Date of Patent: Apr. 29, 1997

[54] DELIVERY SYSTEM FOR AQUEOUS PASTE DENTAL MATERIALS

[75] Inventors: Malcolm W. Wilcox, Woodbury; Thomas W. Martin, Little Canada; Joan V. Brennan, St. Paul, all of Minn.

[73] Assignee: Minnesota Mining and Manufacturing Company, St. Paul, Minn.

[21] Appl. No.: 202,390

[22] Filed: Feb. 28, 1994

[51] Int. Cl.⁶ .................................................. A61C 5/04
[52] U.S. Cl. ........................................................ 433/90
[58] Field of Search .......................... 433/90; 206/63.5, 206/524.4, 524.5, 524.6

[56] References Cited

U.S. PATENT DOCUMENTS

| | | | |
|---|---|---|---|
| 4,212,840 | 7/1980 | Cliff et al. | 264/338 |
| 4,538,920 | 9/1985 | Drake | 366/177 |
| 4,863,072 | 9/1989 | Perler | 433/90 X |
| 4,989,758 | 2/1991 | Keller . | |
| 4,995,540 | 2/1991 | Colin et al. | 433/90 X |
| 5,033,650 | 7/1991 | Colin et al. | 433/90 X |
| 5,100,320 | 3/1992 | Martin et al. . | |
| 5,297,698 | 3/1994 | Martin | 433/90 X |

FOREIGN PATENT DOCUMENTS

| | | |
|---|---|---|
| 0232733 | 11/1989 | European Pat. Off. . |
| 0510211 | 10/1992 | European Pat. Off. . |
| 0563749 | 3/1993 | European Pat. Off. . |

*Primary Examiner*—Nicholas D. Lucchesi
*Attorney, Agent, or Firm*—Gary L. Griswold; Walter N. Kirn; Dale A. Bjorkman

[57] ABSTRACT

A cartridge for delivery of aqueous paste dental materials is provided, wherein the cartridge comprises a cartridge body made from an injection moldable material comprising polyolefin polymers. The cartridge body having a Moisture Permeability less than 25 g mil/m² day atm. and an Oxygen Permeability greater than 180 cm³ mil/m² day atm. The cartridge body comprises at least one chamber adapted for holding and simultaneously dispensing an aqueous paste dental material. The cartridge has a polymerizable aqueous paste dental material contained within the chamber of the cartridge body, and the cartridge is specially adapted to be mounted in a hand-held ejector-type gun.

5 Claims, 4 Drawing Sheets

DELIVERY SYSTEM FOR AQUEOUS PASTE DENTAL MATERIALS

FIELD OF THE INVENTION

The present invention relates to delivery systems for aqueous paste dental materials. More particularly, this invention relates to cartridge bodies for delivery of aqueous paste dental materials using hand-held ejector-type dispensers, and especially for glass ionomer cements.

BACKGROUND OF THE INVENTION

Hand-held ejector-type dispensing systems have long been used for delivery of multiple-part silicone dental impression materials. The standard in the industry has heretofore been use of polypropylene as the material of choice for manufacture of the cartridge body, together with silicone O-rings on the plunger for applying force to extrude the material from the cartridge body. Devices useful for delivery of such materials include multiple barrel dispensing devices having a static mixer provided to efficiently mix the separate components as they are extruded from the barrels of the device. An example of such a device is described in U.S. Pat. No. 4,538,920 to Drake.

U.S. Pat. No. 5,100,320 discloses a cartridge for delivery of dental compositions. The material from which the cartridge is manufactured must have a burst strength greater than that of an otherwise identical cartridge made entirely of polypropylene and a 24 hour water absorption less than nylon-6. These materials are discussed at column 4, lines 3-12.

SUMMARY OF THE INVENTION

Aqueous paste dental materials present particular challenges in delivery systems because these materials possess physical property requirements not experienced before in the dental material delivery art. While the cartridge delivery material art is progressing to stronger materials such as acetal polymers for delivery of dental impression material, it has now been discovered that these new materials do not possess the properties required to provide adequate delivery of aqueous paste dental materials.

The present invention provides a cartridge for delivery of polymerizable aqueous paste dental materials, said cartridge comprising a) a cartridge body made from an injection moldable material comprising a polymer selected from the group consisting of polyolefin polymers, said injection moldable material having a Moisture Permeability less than 25 g mil/m² day atm. and an oxygen permeability greater than 180 cm³ mil/m² day atm., said cartridge body comprising a chamber adapted for holding an aqueous paste dental material and simultaneously dispensing same; and b) a polymerizable aqueous paste dental material comprising a polymerizable component contained within said chamber of said cartridge body; wherein said cartridge is specially adapted to be mounted in a hand-held ejector-type gun.

BRIEF DESCRIPTION OF DRAWING

A preferred embodiment of the invention is illustrated in the accompanying drawing, in which.

DETAILED DESCRIPTION OF PRESENTLY PREFERRED EMBODIMENTS

Figure 1:
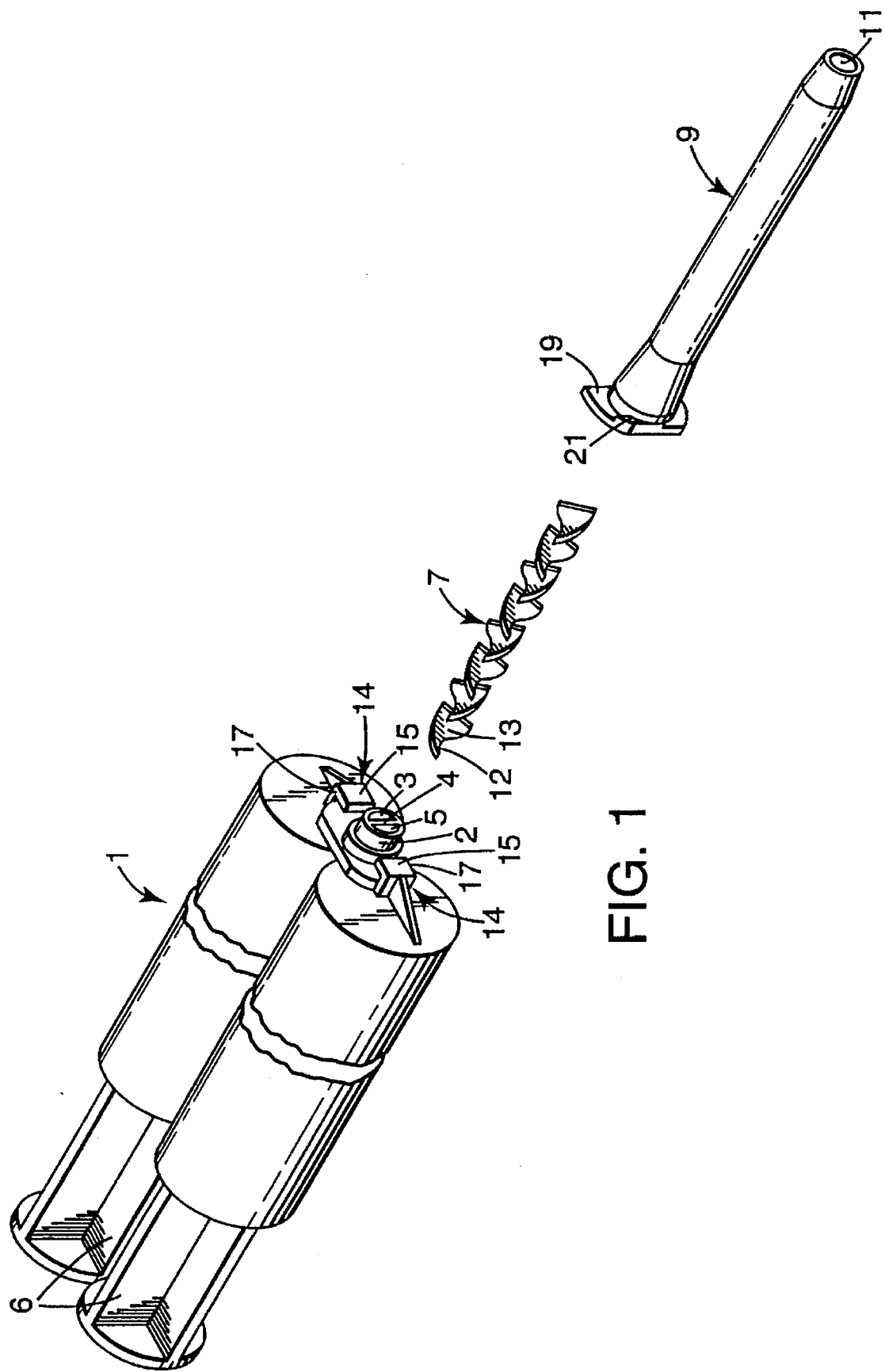
FIG. 1 is an exploded view in perspective of a syringe, static mixing element and exit conduit of this invention.

Recently, advances in the field of glass ionomer cements indicate that a new delivery system for aqueous paste materials for use in the dental industry is desirable. Such advances, for example, are described in pending U.S. patent application Ser. No. (attorney docket no. 50047USA6A), entitled "PASTE:PASTE GLASS IONOMER CEMENT SYSTEM AND METHODS," and pending U.S. patent application Ser. No. (attorney docket no. 50048USA4A), entitled "A METHOD OF IMPROVING THE AQUEOUS-OXIDATIVE STABILITY OF ASCORBIC ACID CONTAINING COMPOSITION," both filed on even date herewith and assigned to the assignee of the present invention, the disclosures of which are expressly incorporated by reference hereto.

The aqueous paste to be contained in the cartridge of the present invention is subject to loss of water through the walls of a cartridge made from the new materials being utilized in the dental industry for storing organic based dental restoratives or silicone based dental impression materials. These cartridge materials are therefore unacceptable for storage of aqueous pastes because they have an unacceptably high moisture permeability. If an aqueous paste were stored in such a moisture permeable cartridge, the paste would suffer serious consistency problems.

In addition to providing a strong moisture barrier for consistency stability, the cartridge must also allow permeation of oxygen to provide polymerization stability. When oxygen fails to penetrate to the polymerizable paste, a reaction starts at the core of the sample, and progresses out to the edges until the entire sample is polymerized.

The cartridge body is made from an injection moldable material comprising a polymer selected from the group consisting of polyolefin polymers. The injection moldable material has a Moisture Permeability less than 25 g mil/m² day atm. Preferably, the injection moldable material has a Moisture Permeability less than 15.5 g mil/m² day atm., and more preferably less than 7 g mil/m² day atm. The injection moldable material has an Oxygen Permeability greater than 180 cm³ mil/m² day atm. Preferably, the injection moldable material has an Oxygen Permeability greater than 380 cm³ mil/m² day atm., and more preferably greater than 1000 cm³ mil/m² day atm. Examples of suitable polyolefin materials useful as a primary component of the injection moldable material include polyethylene, polypropylene, polybutylene and the like. These polymers may be provided in crystalline, semi-crystalline and amorphous states. The polymers may be homopolymers or copolymers with other suitable repeating units, either as random or block copolymers. Optionally, the polymer may be selected from linear, branched, crosslinked, uncrosslinked, fluorinated, hydrogenated or partially hydrogenated olefin polymers. The polymer may also be prepared from a ring-trained cyclic olefin. These polymers may additionally be blended with compatible additional polymers, so long as the material as a whole is injection moldable and has the permeability characteristics required.

The cartridge is preferably integrally molded of a polyethylene such as is sold under the trade name "ALATHON H5618" (from Occidental Chemical Corporation, Dallas, Tex.). Alternatively, the cartridge can be made of an amorphous polyolefin such as is sold under the trade name "ZEONEX" (from Nippon Zeon Co., Ltd., Tokyo, Japan) or a polypropylene resin such as is sold under the trade name "FINA 3467" (from Fina Oil and Chemical Company, Deer Park, Tex.).

The injection moldable material may also optionally comprise a reinforcing filler. Suitable reinforcing fillers include carbon fiber, mica, calcium carbonate, talc, polytetrafluoroethylene, glass (e.g., chopped glass, continuous glass fiber), aluminum flake, mixtures thereof, and the like.

The particular amount of a reinforcing filler that can be used with a material varies from filler to filler and from material to material. Therefore, it is impractical to recite a particular range of filler levels suitable to all fillers and all polymeric materials. In general, however, a filled material can comprise about 10 percent to about 60 percent, preferably 20 percent to about 50 percent, by weight reinforcing filler based on the total weight of the filled material.

Transparent injection moldable materials can be made opaque by coating (e.g., painting or covering with a label) or preferably by incorporating pigments such as titanium dioxide and carbon black, or colorants (e.g., pigments and/or dyes) in order to prevent actinic light from reaching the dental composition contained therein. Colorants can be incorporated into the injection moldable material according to well known methods, e.g., as disclosed in the *Modern Plastics Encyclopedia*, Vol. 65, No. 11, pp. 148–150, McGraw-Hill New York (1988).

A cartridge of the invention is preferably relatively small, and is intended to contain an amount of a dental composition that can be substantially fully expended during the course of a single procedure or several (e.g., 2 to about 10) procedures. A preferred design for a two-part composition delivery system is disclosed in pending U.S. patent application Ser. No. 08/204,989 entitled "DUAL CHAMBER CARTRIDGE DISPENSING SYSTEM FOR DENTAL MATERIAL," filed on even date herewith and assigned to the assignee of the present invention, the disclosure of which is expressly incorporated by reference hereto.

Wall thickness is such that the cartridge will withstand the pressures exerted during extrusion of a dental composition at a useful rate without bursting or excessive yielding. Preferred wall thickness will vary based on several factors, such as the viscosity of the dental composition, the tensile strength of the material from which a cartridge is made, the dimensions of the inner chamber (e.g., length, shape, and cross-sectional area), and the size of the orifice in the discharge nipple.

All non-cartridge body components of the cartridge of the present invention preferably possess at least moisture permeability characteristics, and preferably oxygen permeability characteristics, similar to the cartridge body itself. Thus, the piston also preferably is constructed from a material having a moisture permeability less than 25 g mil/m$^2$ day atm. Preferably, the piston material has a Moisture Permeability less than 15.5 g mil/m$^2$ day atm., and more preferably less than 7 g mil/m$^2$ day atm. While not essential, it is preferred that the piston material have an Oxygen Permeability greater than 180 cm$^3$ mil/m$^2$ day atm. More preferably, the piston material has an Oxygen Permeability greater than 380 cm$^3$ mil/m$^2$ day atm., and most preferably greater than 1000 cm$^3$ mil/m$^2$ day atm.

Surprisingly, the material selection of the O-ring for the piston is significant for protection of the properties of the aqueous paste dental material to be contained within the cartridge body. Even though it represents a small surface area as compared to the balance of the body, the O-ring may allow significant escape of moisture from the aqueous paste. Thus, the O-ring must be selected from elastomeric materials having a moisture permeability less than 25 g mil/m$^2$ day atm. Preferably, the O-ring material has a Moisture Permeability less than 15.5 g mil/m$^2$ day atm., and more preferably less than 7 g mil/m$^2$ day atm. Silicone O-rings, the standard in the industry, have been found to be unacceptable. The O-rings are made from elastomeric rubber, and are preferably made from natural rubber, nitrile rubber, neoprene rubber, ethylene/propylene diamine rubber, butyl rubber or Buna N rubber.

DETAILED DESCRIPTION OF THE DRAWING

Referring now to FIG. 1, there is shown an exploded view in perspective of a cartridge of this invention having a static mixing device located thereon. Syringe 1 has two parallel internal chambers, each of which is intended to be filled with one part of a two-part dental paste material. The chambers in syringe 1 are separated by barrier 4. When a pair of plungers 6 are forced into the chambers in syringe 1, the contents of the syringe exit via outlet 2 through outlet passages 3 and 5, flow through static mixing element 7 and exit conduit 9, and are intimately mixed to form a homogeneous mass which will react following expulsion from outlet 11 of exit conduit 9. Static mixing element 7 is prevented from being expelled during use from the outlet end of exit conduit 9 by a suitable constriction in the inside diameter of exit conduit 9 proximate its outlet end.

Maximum efficiency of mixing is obtained by ensuring that the inlet end 12 of the first mixing blade 13 of static mixing element 7 is generally perpendicular to the plain of contiguity between the two resin streams exiting syringe 1 through exit passages 3 and 5. Such perpendicular orientation is obtained using a locating tang in exit conduit 9, which locating tang serves to orient static mixing element 7 with respect to syringe 1.

Rotational alignment of exit conduit 9 with respect to syringe 1 is obtained using a suitable mounting means (e.g., a bayonet mount). Bayonet locking tabs 14 have locking prongs 15 and stop surfaces 17. Exit conduit 9 has locking ramps 19 and stop surfaces 21. Exit conduit 9 is mounted on syringe. 1 by centering the inlet of exit conduit 9 over outlet 2 of syringe 1, while aligning exit conduit 9 so that it can be pushed between bayonet locking tabs 14. Exit conduit 9 is then inserted firmly over outlet 2, and rotated approximately 90° clockwise (as viewed from the exit end of the conduit) so that locking ramps 19 are wedged between locking prongs 15 and the main body of syringe 1, and stop surfaces 17 engage stop surfaces 21.

When so mounted, exit conduit 9 is fixably rotationally aligned with respect to syringe 1. In addition, through locating means, static mixing element 7 is fixably rotationally aligned with respect to exit conduit 7 and syringe 1. Static mixing element 7 and exit conduit 9 are firmly attached to syringe 1, but can be readily removed and discarded after use by rotating exit conduit 9 approximately 90° counterclockwise (as viewed from the exit end of the conduit) and pulling exit conduit 9 away from syringe 1.

Figure 2:
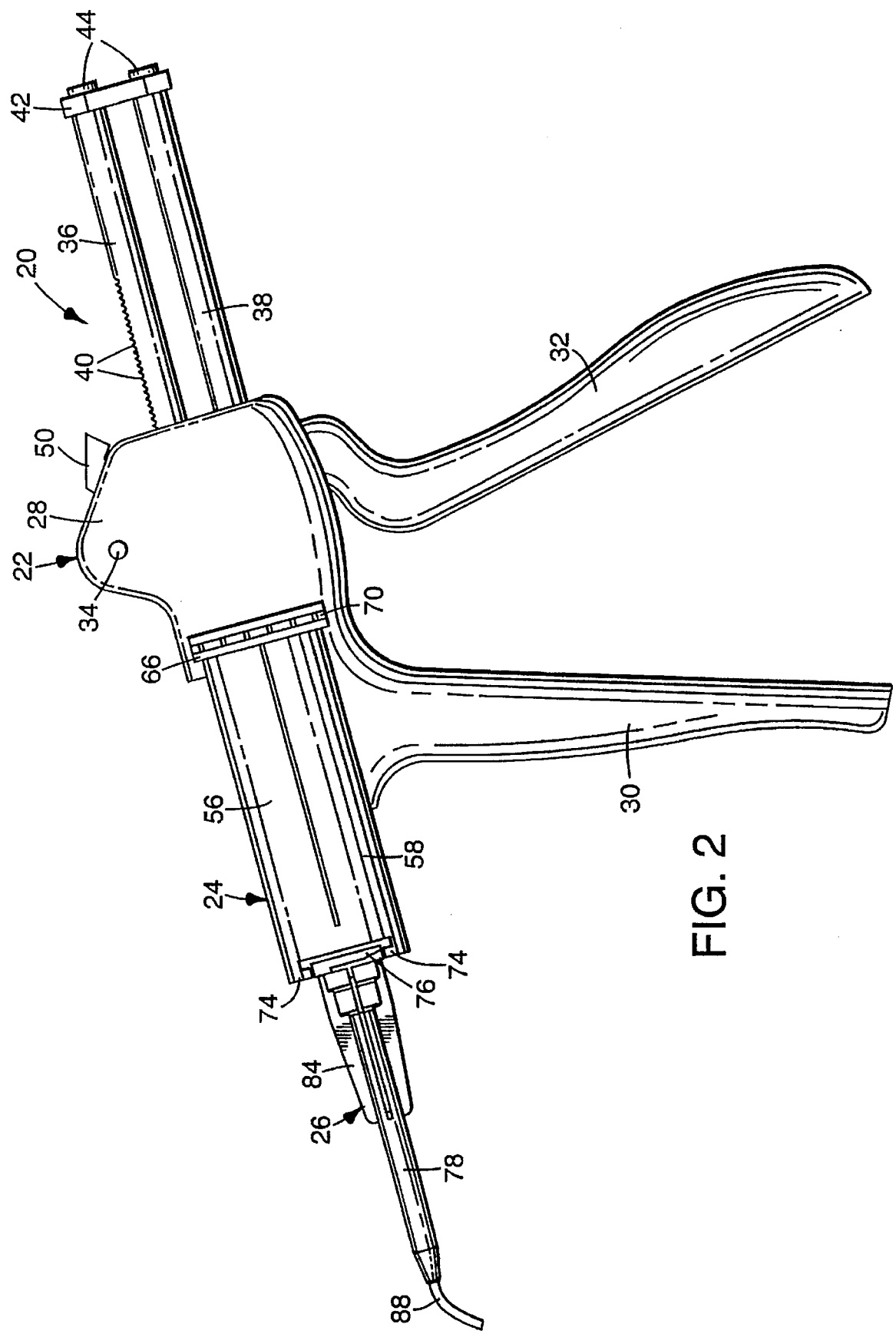
FIG. 2 is a side elevational view of a dispensing system incorporating a cartridge according to the present invention.
Figure 3:
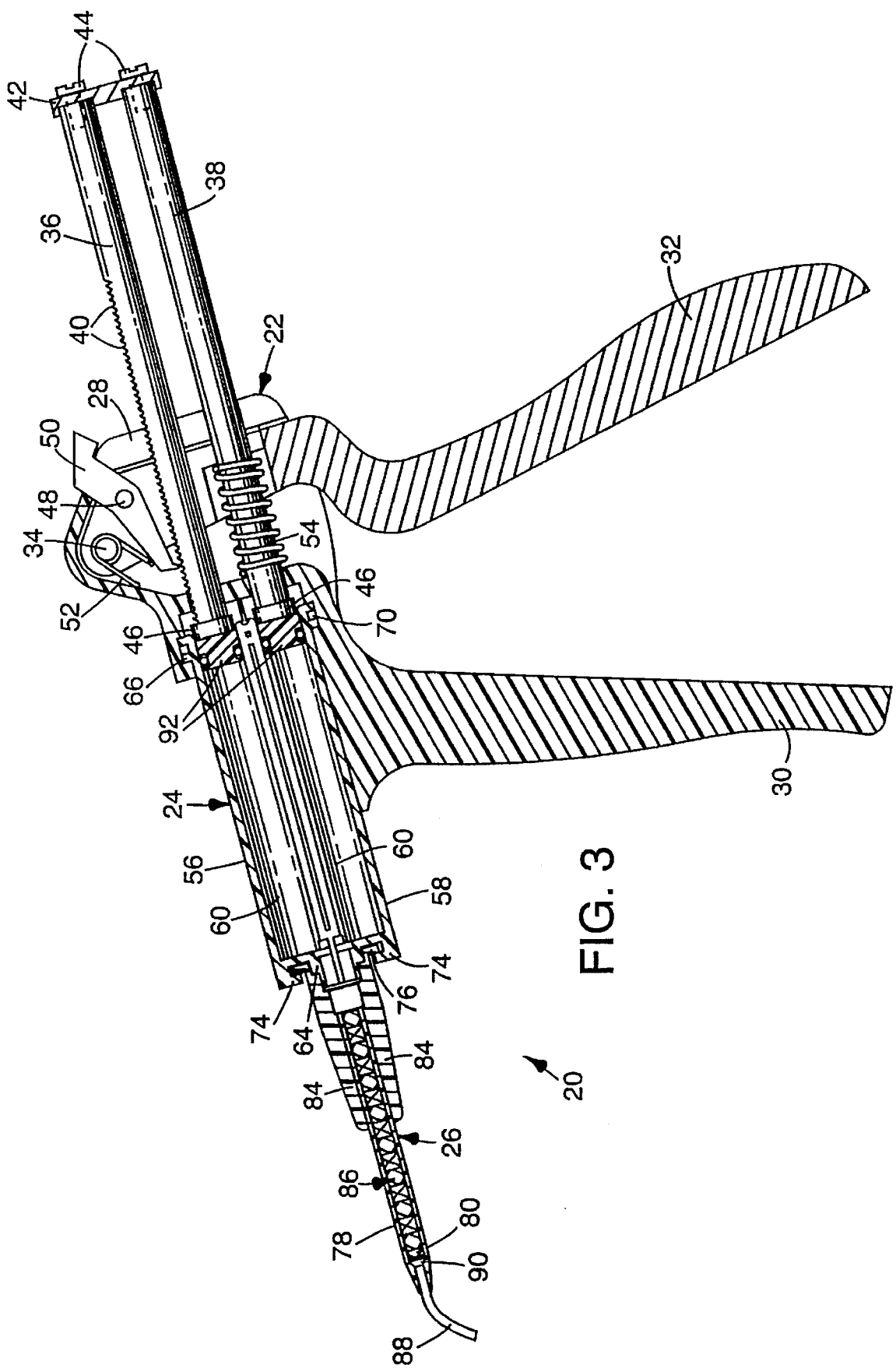
FIG. 3 is a side cross-sectional view of the system shown in FIG. 2.

A dispensing system incorporating a cartridge according to the invention is shown in FIGS. 2–3, and is designated by the numeral 20. The dispensing system 20 broadly includes an applicator 22, a dual chamber dispensing cartridge 24 detachably connected to the applicator 22 and a static mixing assembly 26 that is detachably connected to the front of the cartridge 24.

Turning initially to the applicator 22 in more detail, the applicator 22 includes a hollow body 28 and an elongated, depending handle 30 that is connected to the body 28. The body 28 and the handle 30 are each made in right and left half-sections that are substantially mirror-image of each other, and in each half-section the corresponding portion of the body 28 is integrally molded with the corresponding portion of the handle 30.

The applicator 22 also includes an arm 32 that depends from the body 28 and is located next to the handle 30. An upper portion of the arm 32 is bifurcated and extends within the hollow area of the body 28. A pivot 34, in the form of a cylindrical metal rod, extends transversely between right and left half-sections of the body 28, and pivotally connects the upper bifurcated portion of the arm 32 to the body 28 to thereby enable the arm 32 to move in swinging fashion relative to the handle 30.

The applicator 22 also includes a first elongated plunger 36 and a second elongated plunger 38 that is located below the first plunger 36 in parallel, side-by-side relation. The handle 30 extends at an angle of preferably less than 90 degrees, and more preferably at an angle of about 75 degrees relative to the longitudinal axes of the plungers 36, 38. Both of the plungers 36, 38 have a smooth cylindrical outer surface, except that the top plunger 36 has a top surface with a series of flat teeth 40 that extend along a major extent of the length of the first plunger 36.

The plungers 36, 38 are secured together for simultaneous movement by a rigid block 42 that is connected to the rear end of the plungers 36, 38 by screws 44. The front end of each plunger 36, 38 includes a slightly enlarged cylindrical head 46 (FIG. 3) that is optionally connected to the corresponding plunger 36, 38 by a longitudinally extending screw (not shown in the drawings).

The plungers 36, 38 pass through two respective holes located in a rear wall of the body 28 and also two respective holes located in an interior wall of the body 28 immediately behind the position of the heads 46 that is illustrated in FIG. 3. The enlarged heads 46, being larger than the adjacent holes in the body 28, prevent the plungers 36, 38 from detaching from the body 28 when the plungers 36, 38 are pulled in a rearward direction. Alternatively, the heads 46 could be eliminated, or be made equal in diameter to the plungers 36, 38 so that the latter could be removed from the body 28 if desired.

A second pivot 48, also in the form of a cylindrical metal rod, extends between the bifurcated sections of the upper portion of the arm 32 immediately behind and somewhat below the pivot 34 as shown in FIG. 2. The pivot 48 passes through a hole in a pawl 50 that extends through the space between the bifurcated upper portion of the arm 32. A coil spring 52 is wrapped around the pivot 34 and has an upper leg that bears upwardly against an upper wall of the body 28 and a lower leg that bears downwardly against a forward section of the pawl 50. The spring 52 urges a chisel-shaped lower front edge of the pawl 50 into releasable engagement with one of the teeth 40 of the upper plunger 36.

A coiled compression spring 54 is also located in the hollow area of the body 28. Advantageously, the spring 54 is received around a portion of the lower plunger 38 in order to save space and obviate the need for additional connecting members or the like. The front end of the spring 54 bears against the inner wall of the body 28, while the rear end of the spring 54 bears against a rear end of a slightly enlarged channel constructed in the opposing sections of the upper bifurcated portion of the arm 32 next to the lower plunger 38. The spring 54 urges the arm 32 in a rearward direction and away from the handle 30.

To advance the plungers 36, 38, the arm 32 is swung about pivot 34. As the arm 32 moves toward the handle 30, engagement of the chisel-shaped lower front edge of the pawl 50 with the teeth 40 causes the plungers 36, 38 to simultaneously advance. Upon release of the arm 32, the spring 54 urges the arm 32 to move in a rearwardly direction away from the handle 30; however, frictional engagement of the plungers 36, 38 with the two pairs of holes in the body 28 tend to resist rearward movement of the plungers 36, 38, such that the pawl 50 swings in clockwise direction viewing FIGS. 1 and 2 against the pressure of the spring 52, and enables the chisel-shaped lower front edge to ride over the top of the teeth 40 as the arm 32 moves rearwardly.

A rear, upper end of the pawl 50 extends through a hole in the body 28. When it is desired to move the plungers 36, 38 in a rearwardly direction, such as in instances where the cartridge 24 has been emptied, the user may depress the rear end of the pawl 50 to swing the front edge of the pawl 50 upwardly and disengage the teeth 40. While the pawl 50 is depressed in this manner, the user can grasp block 42 to pull the plungers 36, 38 in a rearwardly direction away from the cartridge 24.

Turning now to the cartridge 24, the cartridge 24 includes a first or upper cylindrical container 56 and a second or lower cylindrical container 58. Both of the containers 56, 58 have an elongated, cylindrical inner chamber 60 with a rear circular opening. The containers 56, 58 (including the longitudinal axes of the chambers 60) lie in parallel, side-by-side and preferably spaced apart relation to each other. Both chambers 60 also have a "D" shaped front opening separated from each other by an inner wall and surrounded by a protruding cylindrical neck 64.

In use of the system 20, the handle 30 is gripped by the fingers of the user while the arm 32 contacts rear portions of the user's palm and an adjacent, opposing section of the user's thumb. As the arm 32 is moved toward the handle 30, the plungers 36, 38 advance and cause the heads 46 to push pistons 92 (FIG. 3) in the chambers 60 in a forwardly direction toward the neck 64. Pistons 92 are provided with O-rings 49 around the circumference of piston 92 and is in sealing conformance with the inner wall of chamber 60. As the pistons 92 advance, components of a dental material that are located in the chambers 60 are expelled from the cartridge 24 and directed through the exit conduit 78, wherein the static mixing element 86 combines the two components to form the uniformly mixed, homogeneous dental material that is then expelled from a front discharge opening of the cannula.

Figure 4:
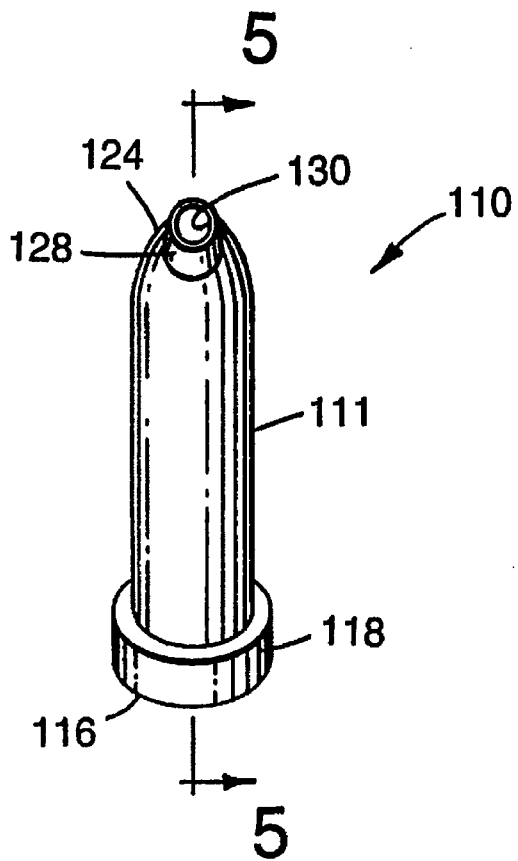
FIG. 4 is a perspective view of a cartridge of the invention.
Figure 5:
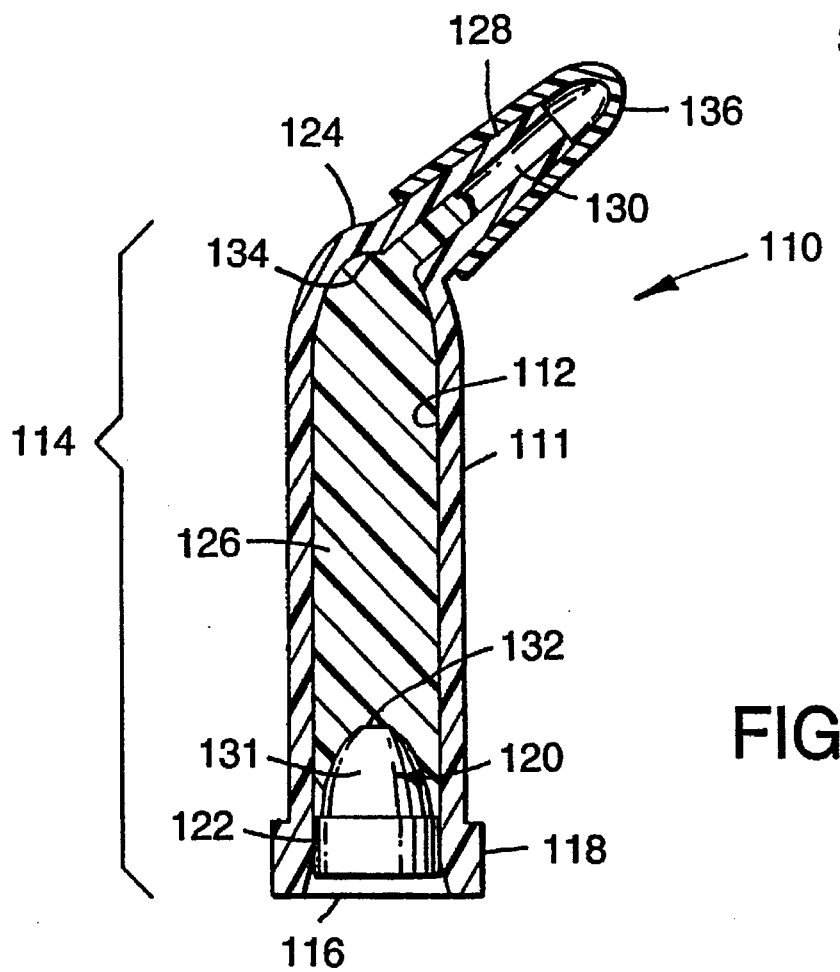
FIG. 5 is a sectional view of the embodiment of FIG. 4 along line 5—5, but including a cap over the discharge nipple.

FIGS. 4 and 5 illustrate embodiment 110 of a cartridge of the invention. Referring to FIG. 5, the illustrated embodiment 110 comprises generally cylindrical inner wall 112 defining elongate inner chamber 114. The body has open end 116 adapted by way of annular flange 118 to be detachably mounted in a hand-held ejector-type gun (not shown).

Displaceable piston 120 is inserted in open end 116. Sidewall 122 of piston 120 is in the form of a flange about the circumference of piston 120 and is in sealing conformance with inner wall 112. Piston 120 serves to seal the open end of the cartridge during storage in order to prevent exposure of enclosed aqueous paste dental material 126 to air. Piston 120 can be displaced toward discharge end 124 of body 110 by means such as a conventional handheld, manually powered, air powered, or motor powered ejector-type gun. When piston 120 is displaced toward discharge end 124, aqueous paste dental material 126 is expressed from discharge nipple 128, which extends from discharge end 124 and has orifice 130 through which the aqueous paste dental material is discharged. Piston 120 has bullet-shaped head 131 with a flattened end 132. The discharge orifice can be sealed with removable cap 136, which serves to seal the discharge end of the cartridge during storage.

For purposes of the present invention, Moisture permeability is to be determined according to ASTM F-1249-90 at 25° C. and 50%RH, and Oxygen permeability is to be determined according to ASTM D-3985 25° C. and 50%RH.

|  | Moisture Permeability[a] | Oxygen Permeability[b] | Oxygen Test Conditions |
|---|---|---|---|
| PTFE (Teflon) | 0.15 | 7750 | 23° C., 50% RH |
| polyester | 24–47 | 74–140 | 23° C. 75% RH |
| Polyethylene (d = 0.96) | 4.65 | 1705 | 23° C. 50% RH |
| Zeonex ™ 250 | 0.16 | 3720 | 25° C. 0% RH |
| Acetal (Delrin ™ 500T) | 29.5 | 186–264 | 23° C. 50% RH |
| THV Fluoroplastic 500(3M) | 3.94 | 2165 | 23° C. |

[a] g mil/m$^2$ day atm.
[b] cm$^3$ mil/m$^2$ day atm.

Cartridges were prepared by injection molding high density polyethylene (Alathon H5618 from Oxychem, Inc.), Zeonex (Zeon Chemicals Company, USA), and Delrin 500T acetal (duPont, Inc.) in a 5 cc Dual Syringe mold. These cartridges were filled with a paste:paste glass ionomer formulation having one aqueous paste comprising the reactive glass and a second paste comprising an organic paste comprising a polymerizable ionomer, and the ends of the cartridges were plugged with polyethylene pistons having butyl rubber O-rings. These filled cartridges were held in a 45° C. oven and the consistency of the paste:paste formulation was checked every three days. The paste:paste formulation in the acetal cartridge dried out in less than three days, while paste:paste formulations of the high density polyethylene and Zeonex cartridges were found to survive the accelerated aging study with minimal adverse effect on the consistency on the paste:paste formulations for more than 12 days.

What is claimed:

1. A cartridge for delivery of aqueous paste dental materials, said cartridge comprising a) a cartridge body made from an injection moldable material comprising a polymer selected from the group consisting of amorphous polyolefin polymers, said cartridge body having a Moisture Permeability less than or equal to about 0.16 g mil/m$^2$ day atm. and an Oxygen Permeability greater than or equal to about 3720 cm$^3$ mil/m$^2$ day atm., said cartridge body comprising at least one chamber adapted for holding an aqueous paste dental material and simultaneously dispensing same; and b) a polymerizable aqueous paste dental material contained within said at least one chamber of said cartridge body;

wherein said cartridge is specially adapted to be mounted in a hand-held ejector-type gun.

2. A cartridge for delivery of multiple-part dental materials, said cartridge comprising a) a cartridge body made from an injection moldable material comprising a polymer selected from the group consisting of amorphous polyolefin polymers, said cartridge body having a Moisture Permeability less than or equal to about 0.16 g mil/m$^2$ day atm. and an Oxygen Permeability greater than or equal to about 3720 cm$^3$ mil/m$^2$ day atm., said cartridge body comprising a plurality of separate chambers adapted for holding separate parts of a multiple-part dental material and simultaneously dispensing same; and b) a polymerizable aqueous paste dental material contained within at least one of said separate chambers of said cartridge body;

wherein said cartridge is specially adapted to be mounted in a hand-held ejector-type gun.

3. The cartridge of claim 2, wherein said aqueous paste dental material is a component of a glass ionomer cement.

4. The cartridge of claim 2, wherein said injection moldable material is a blend of a) an amorphous polyolefin polymer, and b) a second polymer that is compatible with the polymer of (a).

5. The cartridge of claim 1, wherein said injection moldable material is a blend of a) an amorphous polyolefin polymer, and b) a second polymer that is compatible with the polymer of (a).

\* \* \* \* \*